United States Patent [19]

Petro

[11] 3,997,478

[45] Dec. 14, 1976

[54] PROMTED RANEY-NICKEL CATALYSTS

[75] Inventor: Jozsef Petro, Budapest, Hungary

[73] Assignee: Budapesti Muszki Egyetem, Budapest, Hungary

[22] Filed: Sept. 22, 1975

[21] Appl. No.: 615,241

[30] Foreign Application Priority Data

Oct. 7, 1974 Hungary .............................. BU 737

[52] U.S. Cl. ................................ 252/470; 252/471; 252/477 Q

[51] Int. Cl.² .................... B01J 23/84; B01J 23/86; B01J 23/88

[58] Field of Search ............... 252/470, 471, 477 Q

[56] References Cited

UNITED STATES PATENTS

| 3,674,710 | 7/1972 | Richter et al. .................. 252/477 Q |
| 3,712,856 | 1/1973 | Betz ............................... 252/477 Q |
| 3,862,911 | 1/1975 | Chabert ........................... 252/470 |

OTHER PUBLICATIONS

Structure i Fiziko–Khimicheskie Svoistva Skeletnik Katalizatorov, Ispatelstvo Nauka, Kazahskoy SSR, Alma–Ata, 1968, p. 154.

*Primary Examiner*—W. J. Shine

[57] ABSTRACT

The invention relates to new Raney-nickel catalysts containing as promoter at least two metals selected from the group consisting of chromium, cobalt, molybdenum and manganese.

These novel catalysts are far more active than the conventional Raney-nickel catalysts containing no promoter or containing only a single foreign metal.

2 Claims, No Drawings

PROMTED RANEY-NICKEL CATALYSTS

This invention relates to promoted Raney-nickel catalysts. More particularly, this invention relates to Raney-nickel catalysts containing as promoter at least two metals selected from the group consisting of chromium, cobalt, molybdenum and manganese.

As known Raney-nickel catalysts are prepared from alloys containing catalytically active nickel and a catalytically inactive component, such as aluminum or silicon (see U.S. Pat. No. 1,915,473). The catalytically inactive component is leached from the alloy with a solvent (generally with an aqueous alkali) which does not destroy the catalytically active metal. This leaching procedure provides the active metal in the form of a finely divided catalyst.

The investigation of the effects of promoters, such as copper, cobalt, chromium, zirconium and organic metal compounds, exerted on such catalysts, has been started shortly after the elaboration of the first Raney-nickel catalysts. In all of these experiments only a single foreign metal has been added to the nickel. According to the experiences these foreign metals exert frequently a favourable effect on the catalytically active main component (Schroter, R.: Neuere methoden der praparativen organischen Chemie, I., Verlag Chemie, GmbH, Berlin, 1943, pages 80 to 81).

Raney-nickel catalysts containing chromium as promoter has been described in the German patent specification No. 928,407.

The effects of chromium, cobalt and molybdenum exerted separately on Raney-nickel catalysts has been investigated by Paul (Bull. Soc. Chim. France 13, 208 /1946/). In these experiments the amount of the foreign metal related to nickel varied between 1 and 10 % by weight. According to the observations of the author these foreign metals, introduced separately into the catalyst, increase the activity of Raney-nickel in all of the three model reactions investigated. No combinations of foreign metals were studied by the author.

The literature contains only one reference about the examination of the promoter effect appearing when two foreign metals are added simultaneously to Raney-nickel (Strukture i fiziko-khimicheskie svoistva skeletnik katalizatorov, Isdatelstov Nauka, Kazahskoy SSR, Alma-Ata, 1968, p. 154). According to this reference a Raney-nickel catalyst also containing two metals selected from the group consisting of titanium, manganese, vanadium and molybdenum was examined, but no promoter effect was observed.

Now it has been found, unexpectedly, that the activities of Raney-nickel catalysts can be increased to a great extent when at least two metals selected from the group consisting of chromium, cobalt, molybdenum and manganese are added as promoter to these catalysts. The activity-increasing effects of these promoters, when used in combination with each other, exceeds the sum of the effects exerted by the individual promoters.

The new catalysts according to the invention contain the foreign metals, i.e. cobalt, chromium, molybdenum and manganese, respectively, preferably in amounts of 0.2 to 5 %, 0.2 to 5 %, 0.2 to 10 %, and 0.2 to 10 %, respectively, calculated for the weight of the nickel component. It is very surprising that these catalysts have outstandingly high activities, because, on the basis of the earlier publications, no promoter effect could be expected for catalysts containing two or more foreign metals.

The new catalysts according to the invention can be prepared by subjecting an alloy of nickel, at least two foreign metals as defined above, and a metal which can be leached with an alkali (preferably aluminum and/or silicon) to a conventional alkaline leaching operation.

Of the main advantages of the catalysts according to the invention the following are to be mentioned:

a. the new catalysts are far more active than the conventional, non-promoted Raney-nickel catalysts;

b. by varying the amount of the foreign metals (chromium, cobalt, manganese and molybdenum, respectively) and of the catalytically inactive component (aluminum and/or silicon) selective effects can be attained, i.e. catalysts exerting particularly high activities in the hydrogenation of certain pre-determined functional groups (such as carbon-carbon double bonds, nitrile groups, carbonyl groups, nitro groups, etc.) can be obtained; and c. the catalysts with optimum compositions retain their outstandingly high activities for months, i.e. they are stable.

The invention is elucidated in detail by the aid of the following non-limiting Examples.

EXAMPLE 1

50 g. of aluminum, 0.5 g. of chromium, 0.5 g. of molybdenum, 0.5 g. of cobalt and 48.5 g. of nickel are fused, preferably in an induction furnace, the obtained alloy is cooled, and then pulverized by grinding. 1000 g. of the powdery alloy is added in portions into 400 g. of a 25% aqueous sodium hydroxide solution, and after the addition the mixture is heated at 95° to 98° C for 60 minutes. The liquid phase is decanted, 400 ml. of a fresh 25% aqueous sodium hydroxide solution are added, and the mixture is heated at 95° to 98° C for additional 90 minutes. The liquid phase is decanted, and the catalyst is washed until neutral.

EXAMPLE 2

One proceeds as described in Example 1, but an alloy consisting of 50 g. of aluminum, 1.5 g. of chromium, 12 g. of cobalt, 2.5 g. of molybdenum and 45 g. of nickel is used as starting substance.

EXAMPLE 3

One proceeds as described in Example 1, but an alloy consisting of 50 g. of aluminum, 1.5 g. of chromium, 0.25 g. of cobalt, 0.25 g. of molybdenum and 48 g. of nickel is used as starting substance.

EXAMPLE 4

One proceeds as described in Example 1, but an alloy consisting of 50 g. of aluminum, 0.6 g. of chromium, 0.6 g. of cobalt, 2.5 g. of molybdenum and 46.3 g. of nickel is used as starting substance.

EXAMPLE 5

One proceeds as described in Example 1, but an alloy consisting of 50 g. of aluminum, 0.5 g. of cobalt, 3 g. of molybdenum and 46.5 g. of nickel is used as starting substance.

EXAMPLE 6

One proceeds as described in Example 1, but an alloy consisting of 50 g. of aluminum, 2.5 g. of cobalt, 5 g. of molybdenum and 42.5 g. of nickel is used as a starting substance.

EXAMPLE 7

One proceeds as described in Example 1, but an alloy consisting of 50 g. of aluminum, 1 g. of chromium, 0.5 g. of cobalt and 48.5 g. of nickel is used as starting substance.

EXAMPLE 8

One proceeds as described in Example 1, but an alloy consisting of 50 g. of aluminum, 1.5 g. of chromium, 1.5 g. of cobalt and 47 g. of nickel is used as starting substance.

EXAMPLE 9

One proceeds as described in Example 1, but an alloy consisting of 49 g. of aluminum, 1 g. of silicon, 1 g. of chromium, 0.5 g. of molybdenum and 48.5 g. of nickel is used as starting substance.

EXAMPLE 10

One proceeds as described in Example 1, but an alloy consisting of 50 g. of aluminum, 0.25 g. of chromium, 3 g. of molybdenum and 46.75 g. of nickel is used as starting substance.

EXAMPLE 11

One proceeds as described in Example 1, but an alloy consisting of 50 g. of aluminum, 1.5 g. of chromium, 3.5 g. of molybdenum and 45 g. of nickel is used as starting substance.

EXAMPLE 12

One proceeds as described in Example 1, but an alloy consisting of 50 g. of aluminum, 2.5 g. of chromium, 2.5 g. of molybdenum and 45 g. of nickel is used as starting substance.

EXAMPLE 13

One proceeds as described in Example 1, but an alloy consisting of 49 g. of aluminum, 1 g. of silicon, 1.5 g. of chromium, 1.5 g. of molybdenum and 47 g. of nickel is used as starting substance.

EXAMPLE 14

One proceeds as described in Example 1, but an alloy consisting of 50 g. of aluminum, 1.5 g. of chromium, 1.5 g. of molybdenum and 47 g. of nickel is used as starting substance.

EXAMPLE 15

One proceeds as described in Example 1, but an alloy consisting of 50 g. of aluminum, 1.5 g. of chromium, 3 g. of molybdenum and 45.5 g. of nickel is used as starting substance.

EXAMPLE 16

One proceeds as described in Example 1, but an alloy consisting of 50 g. of silicon, 1.5 g. of chromium, 3 g. of molybdenum and 45.5 g. of nickel is used as starting substance.

EXAMPLE 17

One proceeds as described in Example 1, but an alloy consisting of 50 g. of aluminum, 1.5 g. of chromium, 2.0 g. of molybdenum, 3.5 g. of manganese and 43 g. of nickel is used as starting substance.

The activities of the catalysts according to the invention were examined in the hydrogenation of eugenol, acetophenone and benzyl cyanide, respectively. A 10% alcoholic solution of the substrate was hydrogenated in all of the experiments. The measurements were performed at room temperature, under atmospheric pressure, using a shaker rotating with a speed of 160 r.p.m. The activities were expressed as hydrogen uptake (ml) per minute, calculated for 1 g. of active component (nickel + promoters). The results are shown in the following Table.

| No. of Example | Activities | | |
|---|---|---|---|
| | Eugenol | Acetophenone | Benzyl cyanide |
| Non-promoted Raney-nickel | 50 | 3 | 4 |
| & 1 | 82 | 18 | 30 |
| 2 | 84 | 28 | 18 |
| 3 | 106 | 25 | 12 |
| 4 | 110 | 27 | 9 |
| 5 | 100 | 17 | 9 |
| 6 | 97 | 8 | 15 |
| 7 | 120 | 39 | 30 |
| 8 | 92 | 45 | 17 |
| 9 | 94 | 37 | 20 |
| 10 | 126 | 27 | 34 |
| 11 | 139 | 41 | 43 |
| 12 | 94 | 46 | 23 |
| 13 | 97 | 49 | 24 |
| 14 | 93 | 31 | 28 |
| 15 | 98 | 51 | 21 |
| 16 | 138 | 32 | 30 |
| 17 | 120 | 34 | 28 |

What we claim is:

1. A Raney-nickel catalyst containing as promoter at least two metals selected from the group consisting of chromium, cobalt, molybdenum and manganese.

2. A catalyst as claimed in claim 1, containing as promoter at least two metals selected from the group consisting of chromium, cobalt, molybdenum and manganese in an amount of 0.2 to 5 %, 0.2 to 5 %, 0.2 to 10 %, and 0.2 to 10 %, respectively, calculated for the weight of the nickel component.

* * * * *